United States Patent
Shida et al.

(10) Patent No.: US 9,519,967 B2
(45) Date of Patent: Dec. 13, 2016

(54) APPARATUS, METHOD AND OPERATING METHOD OF APPARATUS FOR EXCLUDING NON-TARGET-REGION OF FLUORESCENCE

(71) Applicant: OLYMPUS CORPORATION, Tokyo (JP)

(72) Inventors: Hiromi Shida, Hachioji (JP); Yasushige Ishihara, Hachioji (JP); Satoshi Takekoshi, Hachioji (JP); Kei Kubo, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 68 days.

(21) Appl. No.: 14/312,956

(22) Filed: Jun. 24, 2014

(65) Prior Publication Data
US 2014/0301617 A1 Oct. 9, 2014

Related U.S. Application Data

(63) Continuation of application No. PCT/JP2012/083835, filed on Dec. 27, 2012.

(30) Foreign Application Priority Data

Dec. 28, 2011 (JP) .................. 2011-289877

(51) Int. Cl.
*A61B 1/00* (2006.01)
*A61B 1/04* (2006.01)
(Continued)

(52) U.S. Cl.
CPC ......... *G06T 7/0014* (2013.01); *A61B 1/00009* (2013.01); *A61B 1/043* (2013.01);
(Continued)

(58) Field of Classification Search
None
See application file for complete search history.

(56) References Cited

U.S. PATENT DOCUMENTS 5,749,830 A * 5/1998 Kaneko .............. A61B 1/00082
348/E5.038
6,343,228 B1 * 1/2002 Qu ....................... A61B 5/0084
356/323
(Continued)

FOREIGN PATENT DOCUMENTS

CN 102274000 A1 12/2011
JP 2003-079568 A 3/2003
(Continued)

OTHER PUBLICATIONS

International Search Report dated Feb. 12, 2013 issued in PCT/JP2012/083835.

*Primary Examiner* — Utpal Shah
(74) *Attorney, Agent, or Firm* — Scully, Scott, Murphy & Presser, P.C.

(57) ABSTRACT

Fluorescence generated at a lesion is distinguished from fluorescence generated at portions other than the lesion, and thus, observation is performed by using only the fluorescence generated at the lesion. Provided is a fluorescence observation apparatus including a light radiating portion that radiates excitation light onto an examination subject; a fluorescence-distribution acquiring portion that acquires an intensity distribution of fluorescence generated at the examination subject due to irradiation with the excitation light from the light radiating portion; and a non-target-region excluding portion that, in the fluorescence-intensity distribution acquired by the fluorescence-distribution acquiring portion, excludes regions in which a spectrum in a specific
(Continued)

wavelength band has changed due to a specific biological component whose concentration in a lesion is lower than in other portions.

9 Claims, 15 Drawing Sheets

(51) Int. Cl.
*G02B 21/16* (2006.01)
*G02B 23/24* (2006.01)
*G06K 9/46* (2006.01)
*G06T 7/00* (2006.01)

(52) U.S. Cl.
CPC ......... *G02B 21/16* (2013.01); *G02B 23/2461* (2013.01); *G02B 23/2484* (2013.01); *G06K 9/46* (2013.01); *G06K 2009/4666* (2013.01)

(56) References Cited

U.S. PATENT DOCUMENTS

| 6,537,211 | B1* | 3/2003 | Wang | A61B 1/00009 600/160 |
|---|---|---|---|---|
| 2004/0267091 | A1* | 12/2004 | Imaizumi | A61B 1/0638 600/109 |
| 2005/0027166 | A1* | 2/2005 | Matsumoto | A61B 1/041 600/162 |
| 2006/0173358 | A1* | 8/2006 | Xie | A61B 1/00009 600/476 |
| 2007/0160279 | A1* | 7/2007 | Demos | A61B 5/0071 382/133 |
| 2008/0004495 | A1* | 1/2008 | Allen | A61B 1/043 600/160 |
| 2008/0212867 | A1* | 9/2008 | Provenzano | G01N 33/57415 382/133 |
| 2010/0084563 | A1* | 4/2010 | Ohno | A61B 1/0638 250/363.01 |
| 2010/0245550 | A1* | 9/2010 | Ishihara | A61B 1/0638 348/68 |
| 2010/0245551 | A1* | 9/2010 | Morita | A61B 1/00009 348/68 |
| 2010/0245616 | A1* | 9/2010 | Yoshino | A61B 1/0638 348/223.1 |
| 2010/0322492 | A1* | 12/2010 | Stepp | A61B 1/0638 382/128 |
| 2011/0042580 | A1* | 2/2011 | Wilson | G01N 21/6456 250/458.1 |
| 2011/0118547 | A1* | 5/2011 | Erikawa | A61B 1/00188 600/108 |
| 2011/0313297 | A1* | 12/2011 | Ishihara | A61B 1/00057 600/477 |

FOREIGN PATENT DOCUMENTS

| JP | 2006-191989 A | 7/2006 | |
|---|---|---|---|
| JP | 2007-125245 A | 5/2007 | |
| JP | 2010-069063 A | 4/2010 | |
| JP | 4587811 B | 11/2010 | |
| JP | WO 2011099363 A1 * | 8/2011 | ......... A61B 1/00009 |

* cited by examiner

APPARATUS, METHOD AND OPERATING METHOD OF APPARATUS FOR EXCLUDING NON-TARGET-REGION OF FLUORESCENCE

CROSS-REFERENCE TO RELATED APPLICATIONS

This is a continuation of International Application PCT/JP2012/083835, with an international filing date of Dec. 27, 2012, which is hereby incorporated by reference herein in its entirety. This application claims the benefit of Japanese Patent Application No. 2011-298977, filed on Dec. 28, 2011, the content of which is incorporated herein by reference.

TECHNICAL FIELD

The present invention relates to a fluorescence observation apparatus, a fluorescence observation method, and an operating method of a fluorescence observation apparatus.

BACKGROUND ART

In the related art, there is a known technique with which the presence of an affected area is notified by means of audio, marking, and so forth when the luminance values of pixels in an acquired fluorescence image exceed a predetermined level (for example, see Patent Literature 1).

By doing so, a lesion is identified and a notification about the presence thereof is issued during fluorescence observation, and thus, it is possible to prevent a lesion from being overlooked.

CITATION LIST

Patent Literature

{PTL 1} Publication of Japanese Patent No. 4587811

SUMMARY OF INVENTION

A first aspect of the present invention is a fluorescence observation apparatus including a light radiating portion that radiates excitation light onto an examination subject; a fluorescence-distribution acquiring portion that acquires an intensity distribution of fluorescence generated at the examination subject due to irradiation with the excitation light from the light radiating portion; and a non-target-region excluding portion that excludes, in the fluorescence-intensity distribution acquired by the fluorescence-distribution acquiring portion, regions in which a spectrum in a specific wavelength band has changed due to a specific biological component whose concentration in a lesion is lower than in other portions.

A second aspect of the present invention is a fluorescence observation apparatus including a light radiating portion that radiates excitation light and reference light onto an examination subject; a fluorescence-image acquiring portion that acquires a fluorescence image by capturing fluorescence generated at the examination subject due to irradiation with the excitation light from the light radiating portion; a reference-image acquiring portion that acquires a reference image by capturing return light returning from the examination subject due to irradiation with the reference light from the light radiating portion; a normalized-fluorescence-image generating portion that generates a normalized fluorescence image by dividing the fluorescence image acquired by the fluorescence-image acquiring portion by the reference image acquired by the reference-image acquiring portion; and a non-target-region excluding portion that excludes, in the normalized fluorescence image generated by the normalized-fluorescence-image generating portion, regions in which a spectrum in a specific wavelength band has changed due to a specific biological component whose concentration in a lesion is lower than in other portions.

A third aspect of the present invention is a fluorescence observation method including a radiating step of radiating excitation light onto an examination subject; an acquiring step of acquiring a fluorescence image by capturing fluorescence generated by radiating the excitation light in the radiating step; an excluding step of excluding, in the fluorescence image acquired in the acquiring step, a region in which a spectrum in a specific wavelength band has changed due to a specific biological component whose concentration in a lesion is lower than in other portions; and an identifying step of identifying a specific region having a fluorescence intensity equal to or greater than a predetermined threshold in a region other than the region excluded in the excluding step.

A fourth aspect of the present invention is an operating method of a fluorescence observation apparatus which executes a radiating step of radiating excitation light; an acquiring step of acquiring a fluorescence image by capturing fluorescence generated by radiating the excitation light in the radiating step; an excluding step of excluding, in the fluorescence image acquired in the acquiring step, regions in which a spectrum in a specific wavelength band has changed due to a specific biological component whose concentration in a lesion is lower than in other portions; and an identifying step of identifying a specific region having a fluorescence intensity equal to or greater than a predetermined threshold in a region other than the regions excluded in the excluding step.

DESCRIPTION OF EMBODIMENTS

A fluorescence observation apparatus 1 according to a first embodiment of the present invention will be described below with reference to the drawings.

Figure 1:
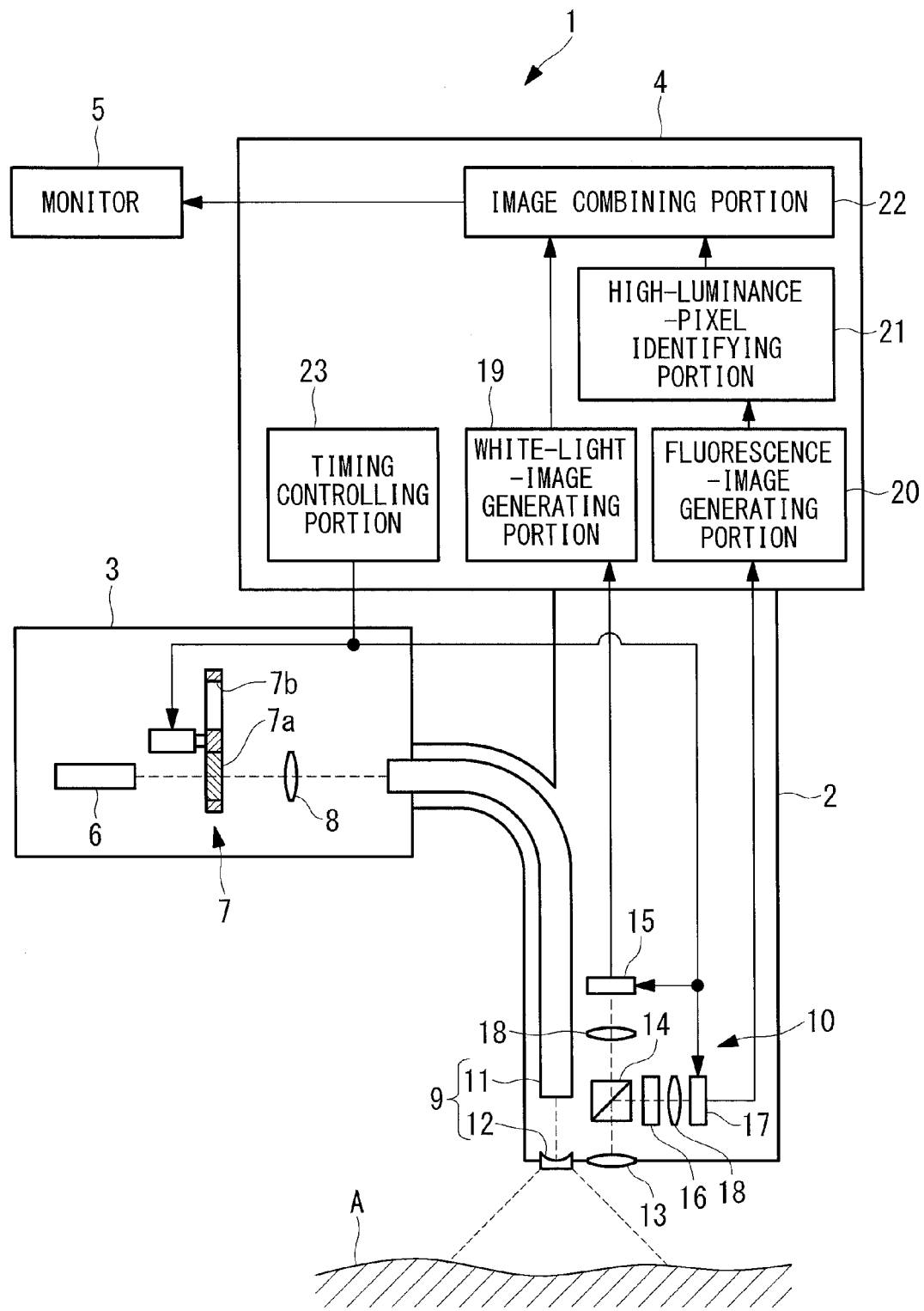
FIG. 1 is a diagram showing the overall configuration of a fluorescence observation apparatus according to a first embodiment of the present invention.

First, the fluorescence observation apparatus 1 according to this embodiment is an endoscope and is provided with, as shown in FIG. 1, an inserted portion 2 that is inserted into a biological subject, a light-source unit 3 and an image processing portion 4 that are connected to the inserted portion 2, and a monitor (display portion) 5 that displays an image generated by the image processing portion 4.

The light-source unit (light radiating portion) 3 is provided with a xenon lamp 6 that emits white light in a wide wavelength band, a filter unit 7 that selects the white light emitted from the xenon lamp 6 or excitation light in a predetermined wavelength band (400 nm to 500 nm) that is extracted from the white light, and a focusing lens 8 that focuses the white light or the excitation light selected by using the filter unit 7 and that makes the focused light enter the inserted portion 2. The filter unit 7 is, for example, a turret that alternately places an excitation filter 7a having high transmittance for the wavelength band from 400 nm to 500 nm and an empty slot 7b on the optical axis of the xenon lamp 6. The filter unit 7 is configured to make the white light and the excitation light alternately enter the inserted portion 2 in a time division manner.

The inserted portion 2 is provided with an illumination optical system 9 that makes the light from the light-source unit 3 exit from the distal end thereof toward an examination subject A and an image-capturing optical system 10 that captures return light coming from the examination subject A.

The illumination optical system 9 is provided with a light-guide cable 11 that is disposed along the inserted portion 2 in the longitudinal direction thereof and that guides the light from the light-source unit 3 to the distal end of the inserted portion 2 and an illumination lens 12 that spreads out the light guided by the light-guide cable 11 and radiates the light onto the examination subject A.

The image-capturing optical system 10 is provided with an objective lens 13 that collects the return light coming from the examination subject A, a splitter 14 that splits the return light collected by the objective lens 13 into two beams, a color CCD (reference-light-image acquiring portion) 15 that captures one of the beams split off from the return light by the splitter 14, a fluorescence filter (non-target-region excluding portion) 16 on which the other beam is made incident, and a monochrome CCD (fluorescence-distribution acquiring portion, fluorescence-image acquiring portion) 17 that captures fluorescence that has passed through the fluorescence filter 16. In the drawings, reference signs 18 indicate focusing lenses.

The splitter 14 is configured so as to split, for example, 90% of the return light collected by the objective lens 13 toward the monochrome CCD 17 and the remaining 10% toward the color CCD 15.

Figure 3:
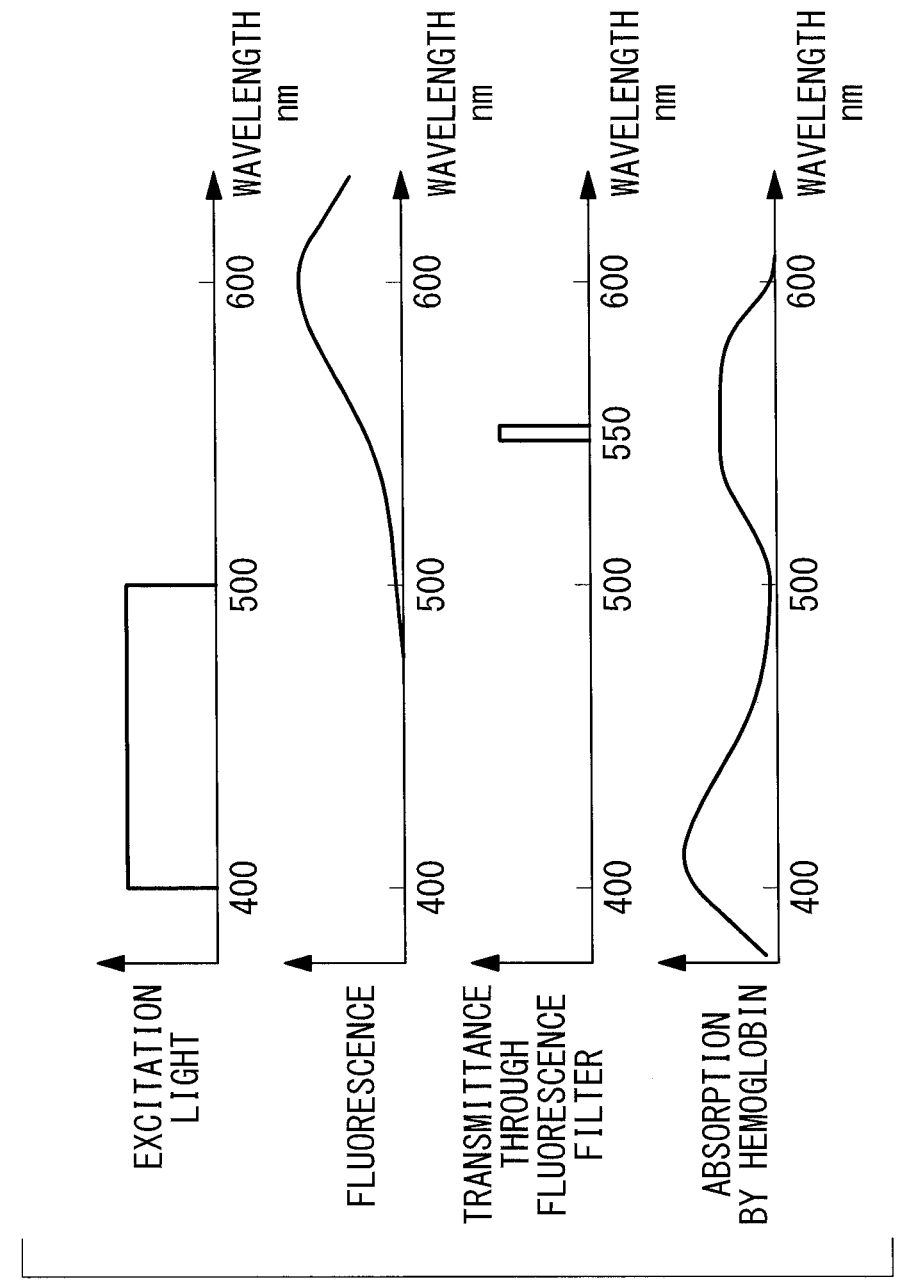
FIG. 3 shows, for the fluorescence observation apparatus in FIG. 1, graphs of wavelength characteristics of excitation light and generated fluorescence, a transmittance characteristic of a fluorescence filter, and an absorption characteristic of hemoglobin.

In this embodiment, as shown in FIG. 3, the fluorescence filter 16 has a transmittance characteristic that allows light in the wavelength band of 550 nm±10 nm to pass therethrough and that blocks light in the other wavelength bands. In other words, the fluorescence filter 16, which is a non-target-region excluding portion, excludes a region in which the spectrum in a specific wavelength band has changed due to a specific biological component whose concentration in a lesion is low. Accordingly, the monochrome CCD 17 acquires a fluorescence-intensity distribution in which fluorescence-emitting regions other than the lesion have been excluded.

Examples of the specific biological component whose concentration in a lesion is low include, hemoglobin, β-carotene, collagen, vitamins, and so forth. In the case of the liver, because numerous capillaries exist therein, the hemoglobin concentration is high. Because hemoglobin exhibits absorption characteristics for wavelength bands equal to or less than 600 nm, the intensity of fluorescence emitted from the liver is greatly decreased in the wavelength band (specific wavelength band) equal to or less than 600 nm due to absorption by hemoglobin. Therefore, by excluding, by means of the fluorescence filter 16, the regions in which the intensity in the wavelength band equal to or less than 600 nm is decreased, it is possible to exclude regions corresponding to the liver from the fluorescence-intensity distribution, and thus, it is possible to acquire a fluorescence-intensity distribution in which fluorescence from a lesion is distributed.

The image processing portion 4 is provided with a white-light-image generating portion (reference-light-image acquiring portion) 19 that generates a white-light image (reference image) from white-light-image information acquired by the color CCD 15, a fluorescence-image generating portion (fluorescence-distribution acquiring portion, fluorescence-image acquiring portion) 20 that generates a fluorescence image from fluorescence-image information acquired by the monochrome CCD 17, a high-luminance-pixel identifying portion (identifying portion, judging portion) 21 that identifies pixels whose luminance values exceed a predetermined threshold from the fluorescence image generated by the fluorescence-image generating portion 20, and an image combining portion 22 that combines the white-light image generated by the white-light-image generating portion 19 and the fluorescence image having the pixels identified by the high-luminance-pixel identifying portion 21.

In addition, the image processing portion 4 is provided with a timing controlling portion 23 so that the filter unit 7 and the two CCDs 15 and 17 are controlled in synchronization. Specifically, the timing controlling portion 23 makes the color CCD 15 capture images in synchronization with the timing at which the empty slot 7b is set in the filter unit 7 and makes the monochrome CCD 17 capture images in synchronization with the timing at which the excitation filter 7a is set in the filter unit 7.

The operation of the thus-configured fluorescence observation apparatus 1 according to this embodiment will be described below.

Figure 2:
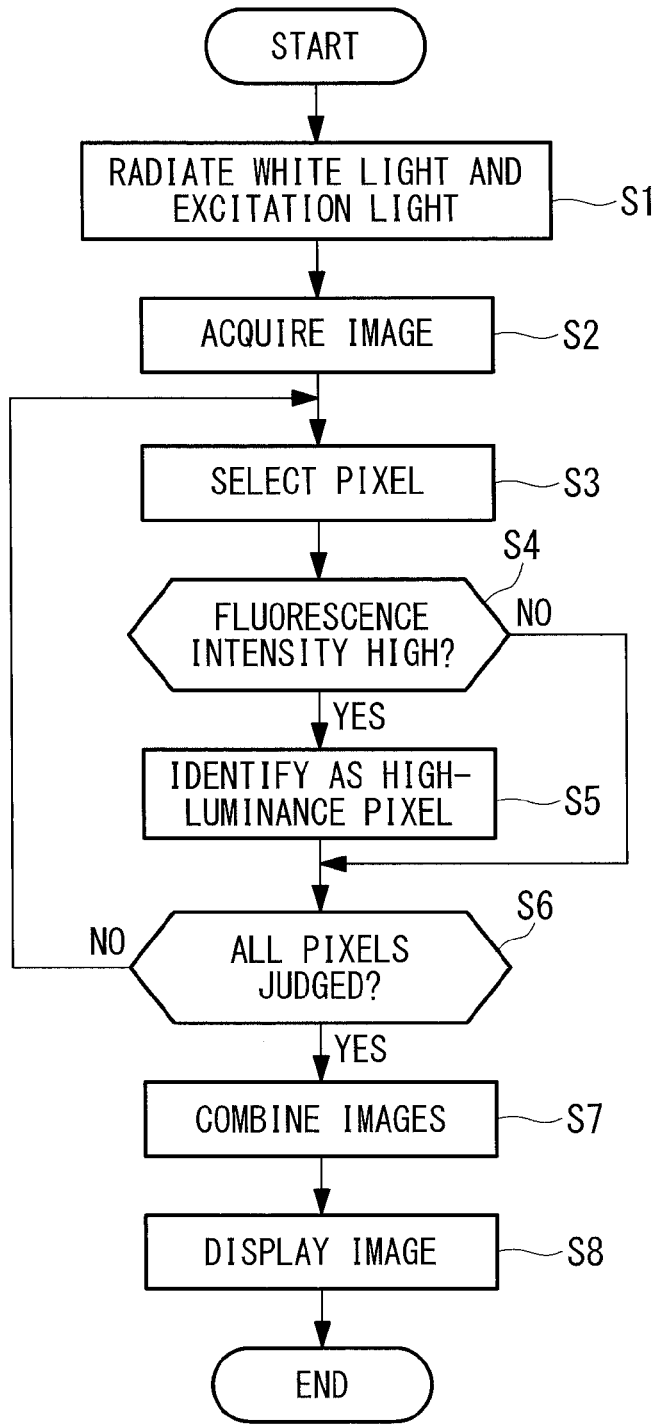
FIG. 2 is a flowchart for explaining processing performed by the fluorescence observation apparatus in FIG. 1.

To observe an organ such as the prostate or the like by using the fluorescence observation apparatus 1 according to this embodiment, as shown in FIG. 2, the light-source unit 3 is activated to supply the inserted portion 2 alternately with the white light and the excitation light that are generated in a time division manner (Step S1). The white light and the excitation light that are made to enter the inserted portion 2 are guided to the distal end of the inserted portion 2 via the light-guide cable 11 of the illumination optical system 9, are spread out by the illumination lens 12, and are radiated onto the examination subject A.

Reflected light that returns from the examination subject A by being reflected at the surface thereof and fluorescence generated by the excitation of a fluorescent substance in the examination subject A due to the excitation light are collected by the objective lens 13 as return light, are split by the splitter 14, are individually focused by the focusing lenses 18, and are captured by the color CCD 15 and the monochrome CCD 17.

The white-light-image information acquired by the color CCD 15 is input to the white-light-image generating portion 19, and a white-light image is generated thereat. In addition, the fluorescence-image information acquired by the monochrome CCD 17 is input to the fluorescence-image generating portion 20, and a fluorescence image is generated thereat (Step S2).

Figure 4:
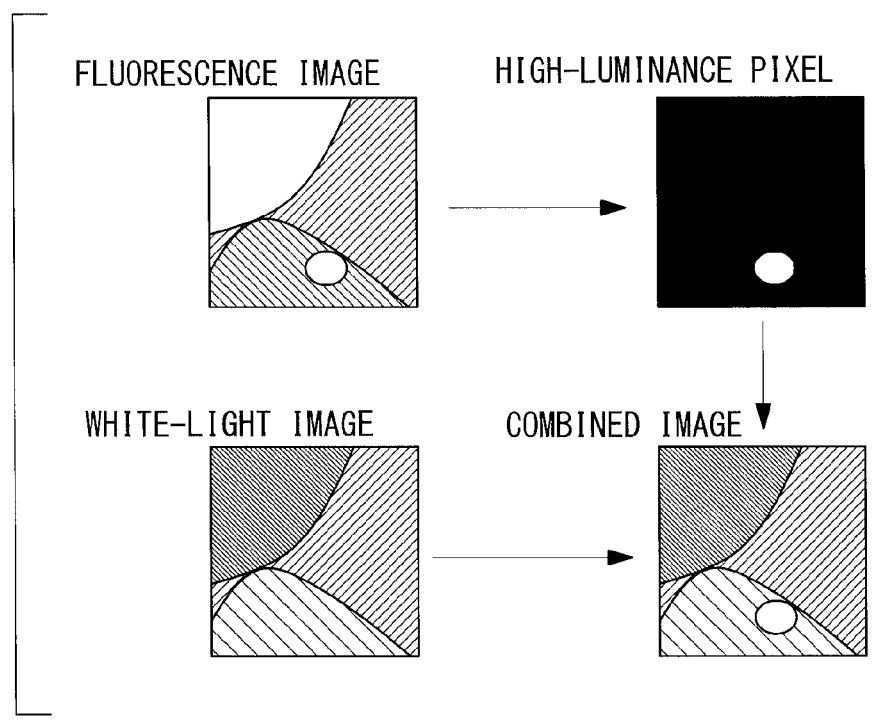
FIG. 4 is a diagram showing examples of a fluorescence image, a high-luminance image, a white-light image, and a combined image that are acquired by the fluorescence observation apparatus in FIG. 1.

In this case, as shown in FIG. 4, because the white-light image is obtained by capturing the reflected light reflected at and returning from the surface of the examination subject A, it is an image that represents morphological characteristics at the external surface of the examination subject A. On the other hand, because the fluorescence is generated at a portion in which a fluorescent substance exists inside the examination subject A, by a fluorescent dye that preferentially accumulates in a tumor such as cancer or the like and that is administered in advance, the fluorescence image becomes an image that has high luminance in the cancer tissue.

However, in an organ where a large amount of blood accumulates, like the liver, the fluorescent dye that preferentially accumulates in the cancer tissue also accumulates therein due to the metabolism, which consequently causes fluorescence generation therein when irradiated with the excitation light.

In this embodiment, the return light that has been split by the splitter 14 toward the monochrome CCD 17 is made incident on the fluorescence filter 16, and thus, only the fluorescence in the wavelength band of 550 nm±10 nm passes through the fluorescence filter 16 and is captured by the monochrome CCD 17.

Because this wavelength band of 550 nm±10 nm is the wavelength band in which absorption by hemoglobin occurs, it is not possible to achieve a desired fluorescence intensity when blood exists. Therefore, the case in which the fluorescence intensity is less than the predetermined threshold can be judged as indicating fluorescence from an organ other than cancer tissue, such as the liver or the like, and the case in which the predetermined threshold is reached or exceeded can be judged as indicating fluorescence from cancer tissue.

Therefore, in this embodiment, for the fluorescence image generated by the fluorescence-image generating portion 20, the high-luminance-pixel identifying portion 21 of the image processing portion 4 sequentially selects pixels (Step S3), judges whether or not the pixels have luminance values that exceed the predetermined threshold (Step S4), and, in the case in which the luminance values exceed the threshold, identifies the pixels as high-luminance pixels (Step S5). By doing so, the high-luminance-pixel identifying portion 21 identifies a specific region in which regions other than a lesion are excluded from a region in which fluorescence is being generated and in which the fluorescence intensity thereof is equal to or greater than the predetermined threshold. Then, it is judged whether or not all pixels have been subjected to identification (Step S6), and, in the case in which identification for all pixels has been completed, the image combining portion 22 combines the fluorescence image based on the identified pixels and the white-light image (Step S7).

By doing so, it is possible to display the fluorescence image showing cancer tissue or the like on the monitor 5, superimposed on the white-light image showing the morphological characteristics in the observation area (Step S8). Because the fluorescence from an organ or the like other than the cancer tissue has been excluded from this combined image, there is an advantage in that it is possible to clearly indicate the position of the cancer tissue by clearly distinguishing it from the liver or the like. In other words, the fluorescence generated at a lesion can be distinguished from the fluorescence generated at portions other than the lesion, and thus, observation can be performed based only on the fluorescence generated at the lesion.

Note that, in this embodiment, a fluorescence image is generated by providing the fluorescence-image generating portion 20, and, by using this fluorescence image, a fluorescence image constituted of pixels having intensities that exceed the predetermined threshold is combined with the white-light image; alternatively, however, without providing the fluorescence-image generating portion 20, the fluorescence information transmitted from the monochrome CCD 17 may be sequentially compared with the predetermined threshold, and a region may be constituted of pixels having intensities that exceed the predetermined threshold.

Next, a fluorescence observation apparatus 1' according to a second embodiment of the present invention will be described below with reference to the drawings.

In describing the fluorescence observation apparatus 1' according to this embodiment, portions whose configurations are the same as those of the fluorescence observation apparatus 1 according to the first embodiment described above are assigned the same reference signs, and descriptions thereof will be omitted.

Figure 5:
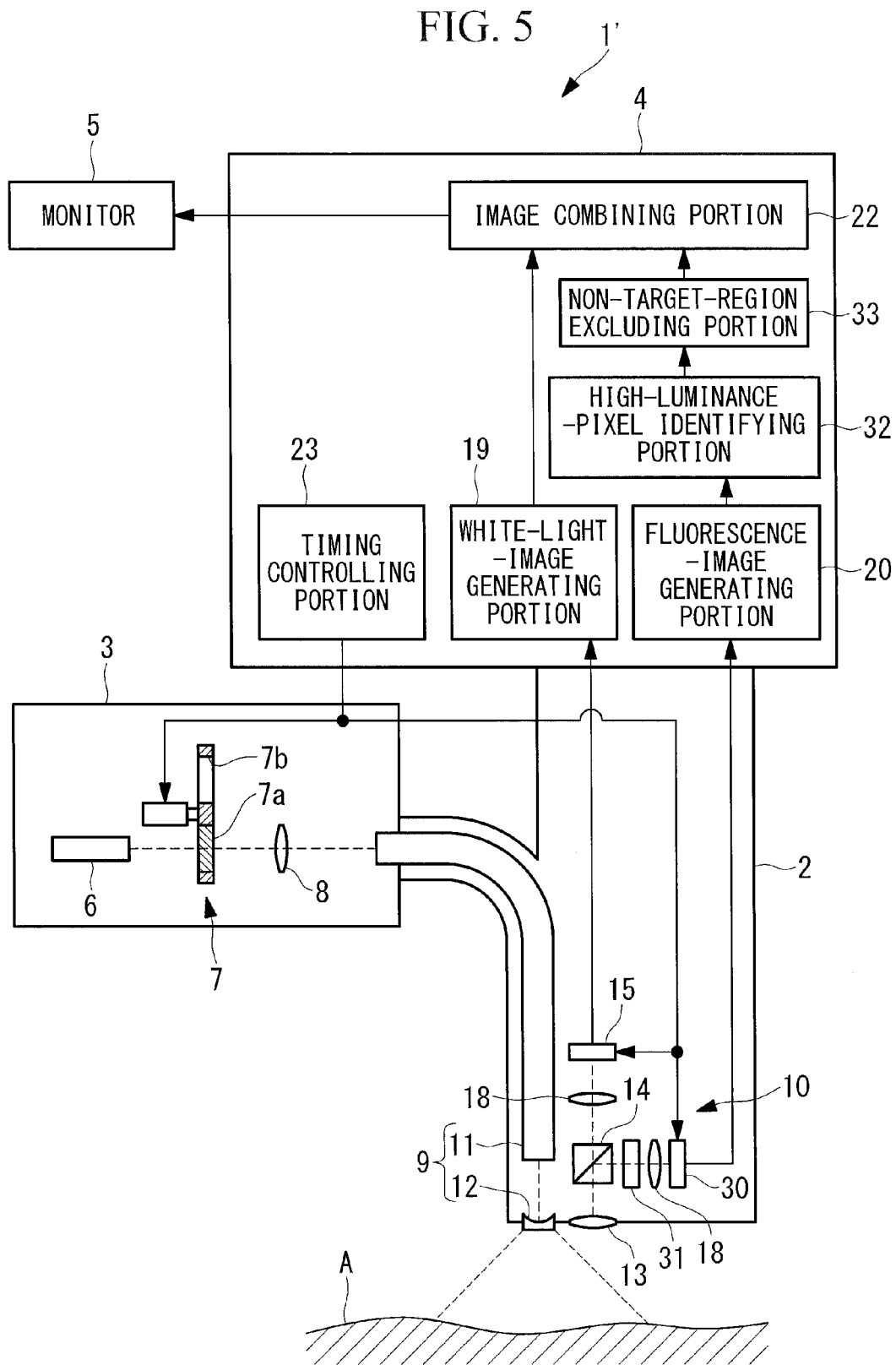
FIG. 5 is a diagram showing the overall configuration of a fluorescence observation apparatus according to a second embodiment of the present invention.
Figure 7:
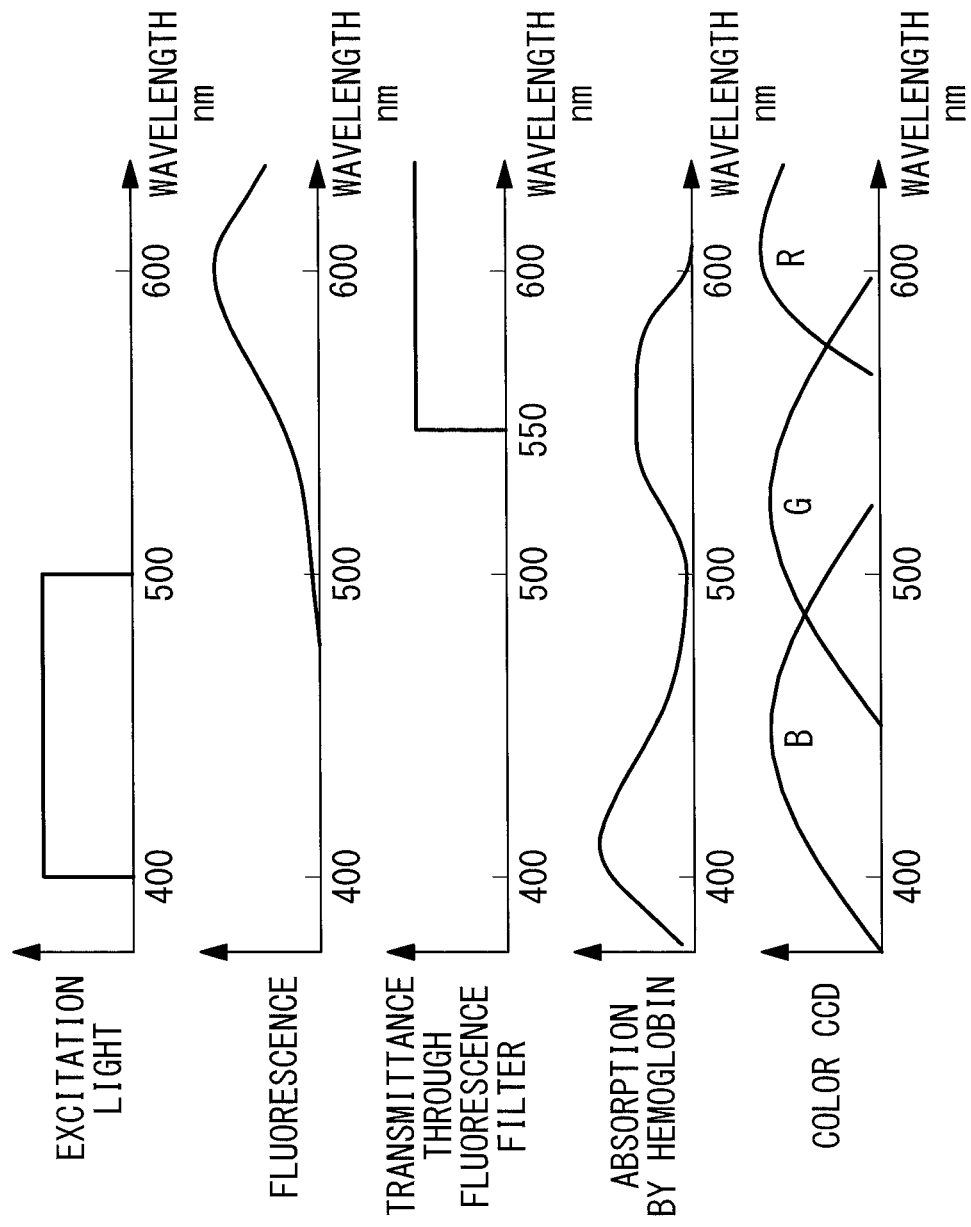
FIG. 7 shows, for the fluorescence observation apparatus in FIG. 5, graphs of wavelength characteristics of excitation light and generated fluorescence, a transmittance characteristic of a fluorescence filter, an absorption characteristic of hemoglobin, and a wavelength characteristic of a color CCD.

As shown in FIG. 5, in the fluorescence observation apparatus 1' according to this embodiment, a color CCD (fluorescence-distribution acquiring portion, fluorescence-image acquiring portion) 30 is employed as an imaging device for capturing fluorescence images and, as shown in FIG. 7, a filter having a transmission band equal to or greater than 550 nm is employed as a fluorescence filter 31. The color CCD 30 employs, for example, a so-called Bayer array in which 4-pixel unit pixel groups are repeatedly arrayed, each of the unit pixel groups being composed of two rows and two columns in which one filter that allows light in the red wavelength band to pass therethrough, two filters that allow light in the green wavelength band to pass therethrough, and one filter that allows light in the blue wavelength band to pass therethrough are disposed.

In addition, in this embodiment, the image processing portion 4 is provided with a high-luminance-pixel identifying portion 32 that identifies, in the fluorescence image generated by the fluorescence-image generating portion 20, high-luminance pixels in which the sum of green and red luminance values of the individual unit pixel groups exceeds a first threshold SH1 and a non-target-region excluding portion 33 that identifies, among the unit pixel groups identified by the high-luminance-pixel identifying portion 32, the unit pixel groups in which the green luminance values exceed a second threshold SH2.

Figure 6:
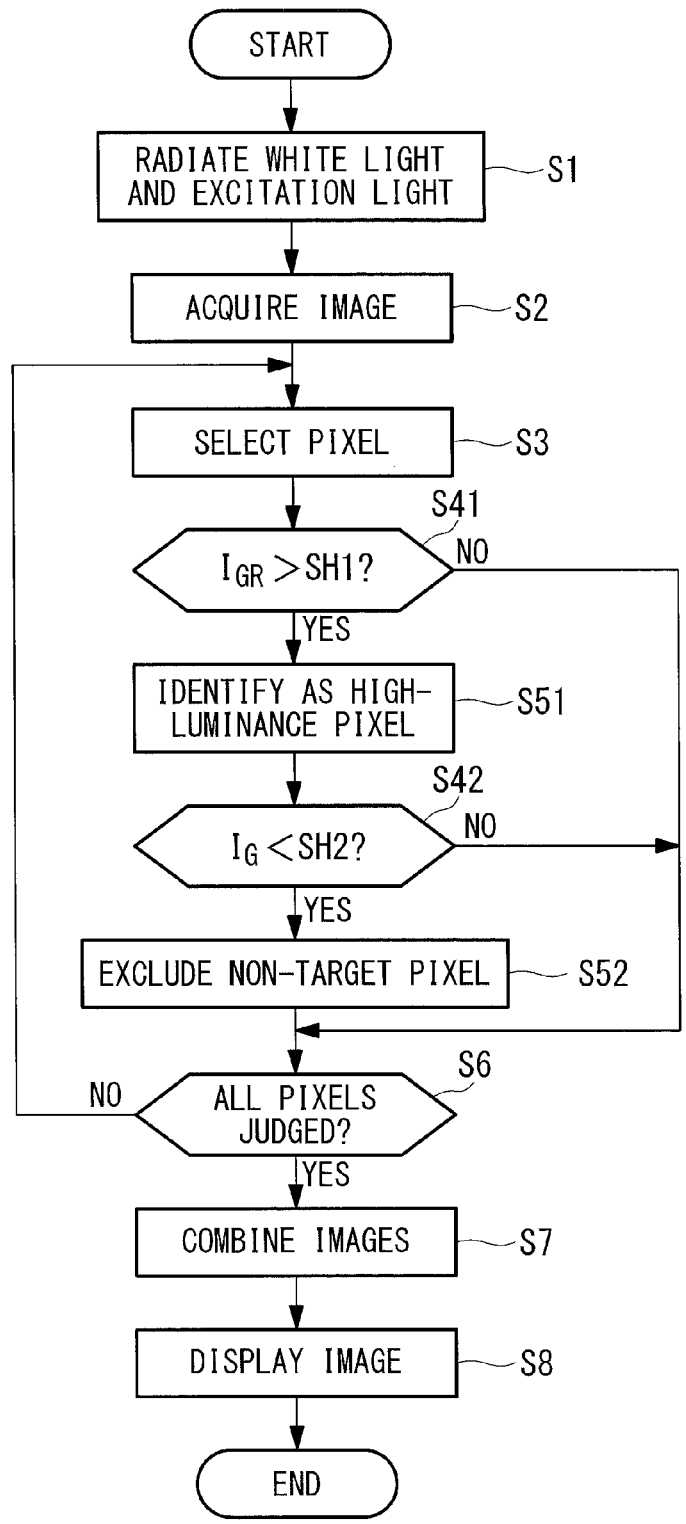
FIG. 6 is a flowchart for explaining processing performed by the fluorescence observation apparatus in FIG. 5.

With the thus-configured fluorescence observation apparatus 1' according to this embodiment, of the fluorescence generated at the examination subject A, light in the wavelength band less than 550 nm is blocked by the fluorescence filter 31, and only the fluorescence in the wavelength band equal to or greater than 550 nm is captured by the color CCD 30. As shown in FIG. 6, for the light that has entered the color CCD 30, the sum of intensities of light that is made incident on the pixels provided with the green filters and the red filter is calculated at the high-luminance-pixel identifying portion 32 for each unit pixel group, and, subsequently, that summed intensity $I_{GR}$ is compared with the first threshold SH1 (Step S41). The unit pixel groups for which the summed intensity $I_{GR}$ exceeds the first threshold SH1 are identified as the high-luminance pixels (Step S51).

Furthermore, for the individual unit pixel groups identified as the high-luminance pixels by the high-luminance-pixel identifying portion 32, the intensities $I_G$ of light that has been made incident on the pixels provided with the green filters are compared with a second threshold SH2 at the non-target-region excluding portion 33 (Step S42). Regions in which the intensities $I_G$ of the green light are less than the second threshold SH2 are, in other words, regions in which absorption by hemoglobin is occurring, and because these regions can be judged to be non-target regions, such as organs or the like other than cancer tissue, these regions are excluded at the non-target-region excluding portion 33 (Step S52).

As has been described above, with the fluorescence observation apparatus 1' according to this embodiment, of the fluorescence generated at the examination subject A, regions in which the summed intensities $I_{GR}$ of fluorescence in the green and red wavelength bands are greater than the first threshold SH1 constitute the high-luminance regions that are finally combined with the white-light image; therefore, there is an advantage in that, even in the case of fluorescence observation in which weak fluorescence levels are observed, noise can be reduced, and high-precision observation can be performed.

Note that, with the fluorescence observation apparatus 1' according to this embodiment, first, the summed intensities $I_{GR}$ of the fluorescence in the green and the red wavelength bands are compared with the first threshold SH1, thus identifying pixels in which the summed intensities $I_{GR}$ are greater than the first threshold SH1, and, subsequently, pixels in which the intensities $I_G$ of the fluorescence in the green wavelength band are less than the second threshold SH2 are excluded from the identified pixels. Alternatively, the processing of comparing the summed intensities $I_{GR}$ of fluorescence in the green and red wavelength bands with the first threshold SH1 and the processing of comparing the intensities $I_G$ of the fluorescence in the green wavelength band with the second threshold SH2 may be performed in parallel or in an arbitrary order, and pixels in which the summed intensities $I_{GR}$ of fluorescence in the green and red wavelength bands are greater than the first threshold SH1 and the intensities $I_G$ of fluorescence in the green wavelength band are greater than the second threshold SH2 may be identified as the high-luminance regions.

Next, a fluorescence observation apparatus 1" according to a third embodiment of the present invention will be described with reference to the drawings.

In describing this embodiment, portions whose configurations are the same as those of the fluorescence observation apparatuses 1 and 1' according to the first and second embodiments described above are assigned the same reference signs, and descriptions thereof will be omitted.

Figure 8:
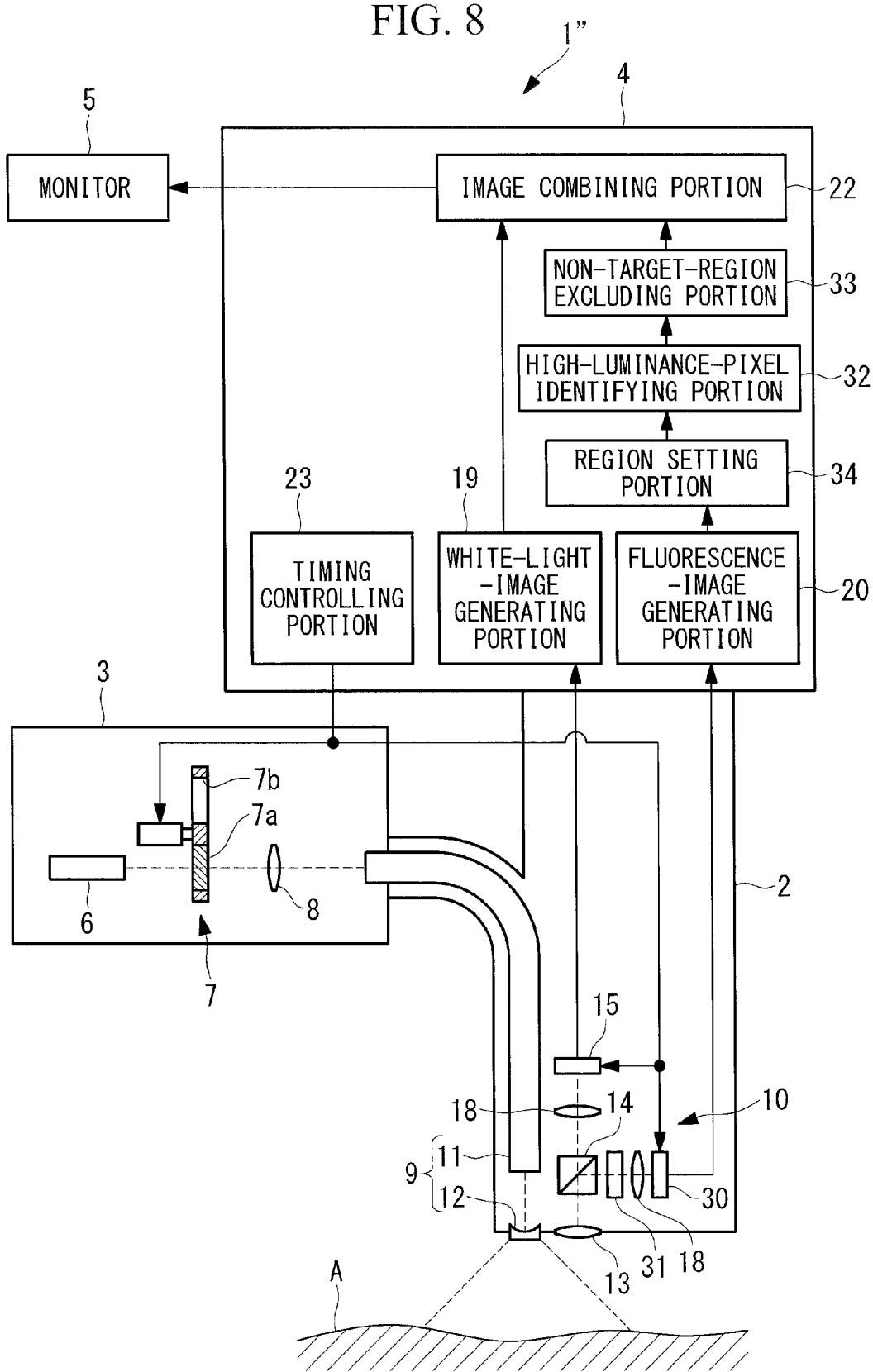
FIG. 8 is a diagram showing the overall configuration of a fluorescence observation apparatus according to a third embodiment of the present invention.

As shown in FIG. 8, the fluorescence observation apparatus 1" according to this embodiment differs from the fluorescence observation apparatuses 1 and 1' according to the first and second embodiments in that the high-luminance-pixel identifying portion does not perform identification for all pixels that are arrayed in rows and columns when identifying high-luminance pixels in a fluorescence image generated by the fluorescence-image generating portion.

The fluorescence observation apparatus 1" according to this embodiment is provided with a region setting portion 34 that sets small regions that serve as candidates for the high-luminance pixels, and the high-luminance-pixel identifying portion 32 identifies the high-luminance pixels only in the candidate small regions set by the region setting portion 34.

Figure 9:
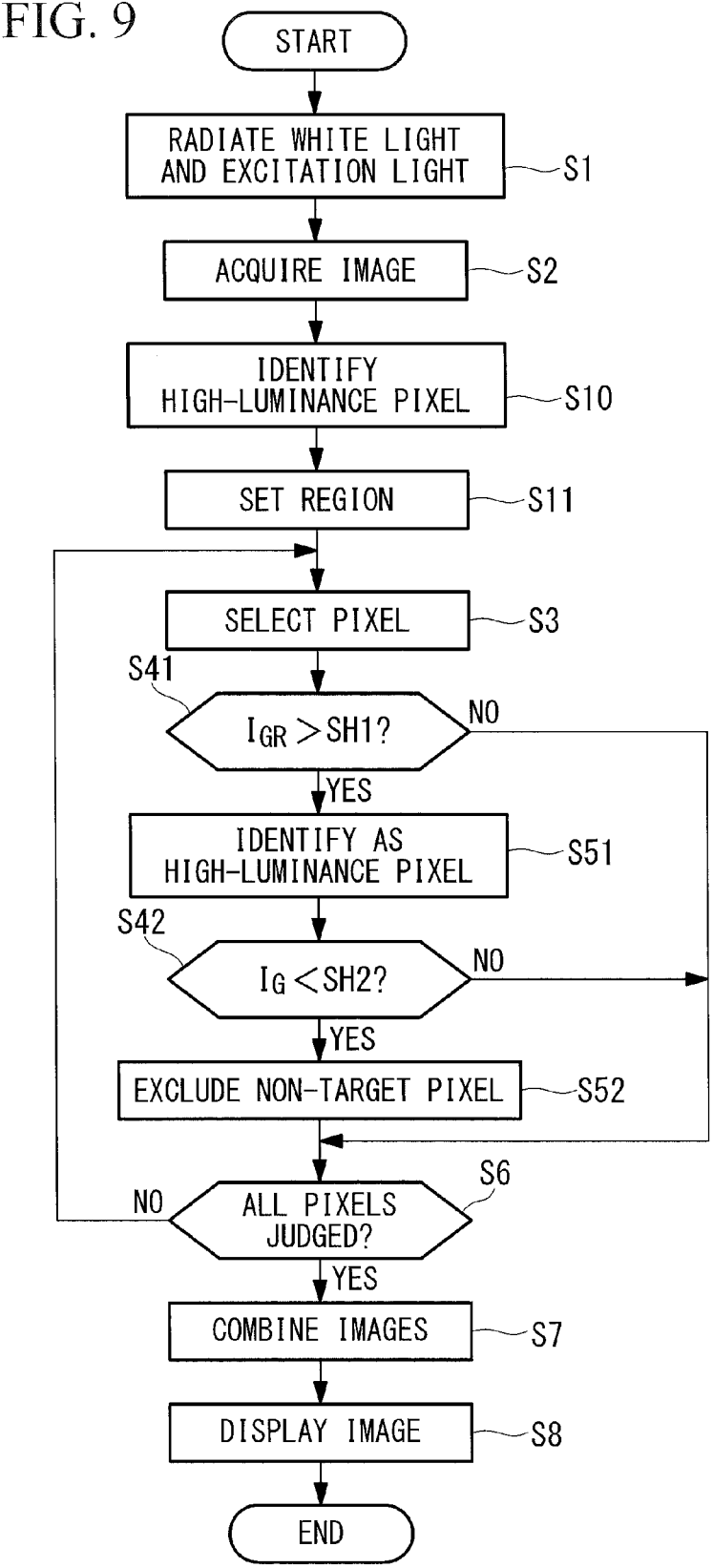
FIG. 9 is a flowchart for explaining processing performed by the fluorescence observation apparatus in FIG. 8.

More specifically, as shown in FIG. 9, the region setting portion 34 performs processing for identifying high-luminance pixels in every three rows in a fluorescence image generated by the fluorescence-image generating portion 20 (Step S10), processing for setting small regions formed of, for example, 7×7 pixel groups centered around all identified high-luminance pixels (Step S11), and processing for identifying high-luminance pixels in the set small regions in the same manner as in the first embodiment or the second embodiment (Steps S3 to S6).

Figure 10A:
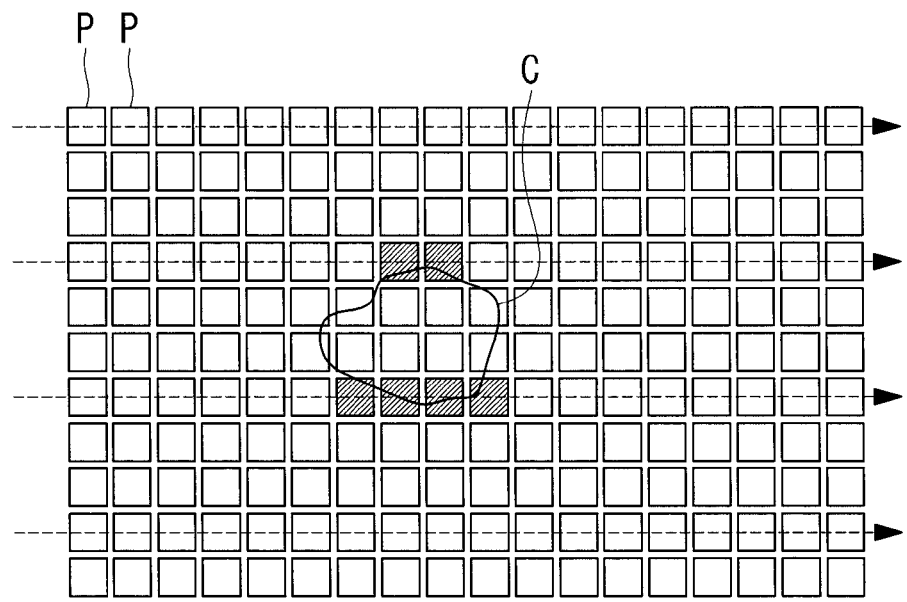
FIG. 10A is a diagram for explaining processing for detecting high-luminance pixels, which is performed by a region setting portion of the fluorescence observation apparatus in FIG. 8.

Here, it is assumed that the pixel pitch of the color CCD (imaging device) 30 is about 3 μm and that a minimum size of cancer tissue C to be identified corresponds to a 4×4 pixel area. Accordingly, as shown in FIG. 10A, when some pixels in some rows are identified as the high-luminance pixels (pixels indicated by hatching), the cancer tissue C is included in 7×7 pixel groups centered around the identified pixels even if the cancer tissue C has the minimum size. Therefore, as shown in FIG. 10B, by setting these small regions (regions indicated by hatching) as candidates, the cancer tissue C can be detected without missing any portion thereof.

In Step S10, in a first fluorescence image generated by the fluorescence-image generating portion 20, the region setting portion 34 treats rows consisting of 2×2 unit pixel groups P that constitute the color CCD 30 as one row, and identifies, for the individual unit pixel groups P in the rows that are selected every three rows, high-luminance pixels in which summed intensities of fluorescence in the green and red wavelength bands in the individual unit pixel groups P exceed the first threshold and, subsequently, pixels in which intensities of fluorescence in the green wavelength band are less than the second threshold are excluded from the identified high-luminance pixels.

Figure 10B:
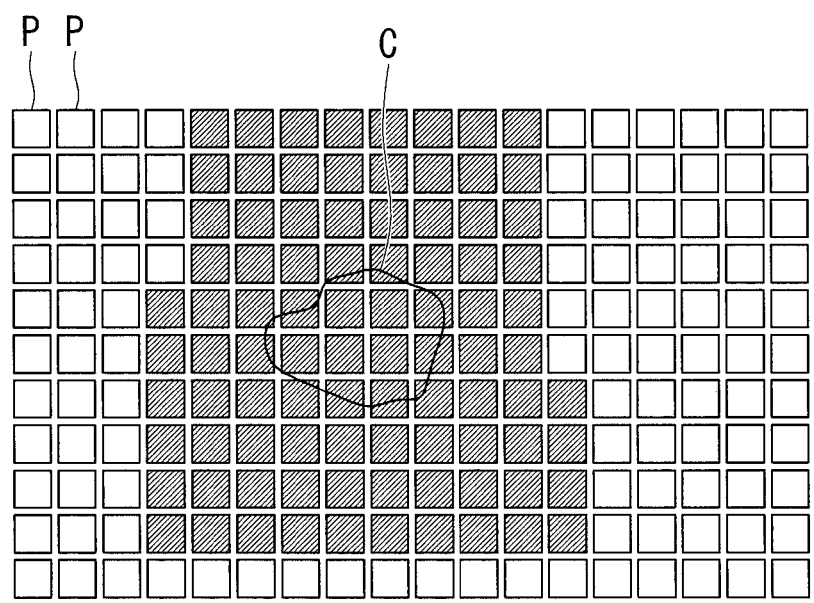
FIG. 10B is a diagram for explaining processing for setting a small region, which is performed by the region setting portion of the fluorescence observation apparatus in FIG. 8.

When any of the unit pixel groups P is identified in this way, as indicated by hatching in FIG. 10A, 7×7, that is, 49, unit pixel groups P centered around these unit pixel groups P are set as small regions targeted for identification, as indicated by hatching in FIG. 10B. This processing is performed every three rows for all unit pixel groups P in the individual rows.

By doing so, because small regions that include the entire cancer tissue C and that are larger than the cancer tissue C are identified, as shown in FIG. 10B, in these small regions, high-luminance pixels in which the summed intensities $I_{GR}$ of fluorescence in the green and red wavelength bands exceed the first threshold SH1 are identified again, and, subsequently, pixels in which the intensities $I_G$ of fluorescence in the green wavelength band are less than the second threshold SH2 are excluded from the identified high-luminance pixels.

As described above, with the fluorescence observation apparatus 1" according to this embodiment, because the high-luminance pixels are identified only in the small regions in which the presence of the cancer tissue C is confirmed instead of judging whether or not all pixels are high-luminance pixels or not, it is possible to reduce the image processing load. In addition, because the time required for identifying the high-luminance pixels is reduced, it becomes possible to quickly display a combined image, and thus, it is possible to smoothly display a combined image in real-time. By doing so, it is possible to enhance the ease of observation, and it is possible to enhance the efficiency and precision of cancer tissue detection.

In particular, in the case of cancer tissue C in an early stage, because the cancer tissue C existing in an image-capturing area would be extremely small, it is highly wasteful to apply image processing to all pixels. In contrast, with this embodiment, because the presence/absence of cancer tissue C is judged every three rows, and identification of high-luminance pixels is subsequently performed in detail for regions that have been judged to include the cancer tissue C, there is less waste, and thus, it is possible to reduce the processing load.

Note that, in this embodiment, although the high-luminance pixels are identified every three rows, the number of rows to be skipped when performing identification may be arbitrarily set depending on the pixel pitch and the size of cancer tissue C or the like that needs to be detected. In addition, instead of performing identification every three rows, identification may be performed every three columns.

In the individual embodiments described above, the white light and the excitation light are radiated onto the examination subject A in a time division manner, and the white-light image, which serves as a reference image, and the fluorescence image are generated at the same time; alternatively, however, a reference image and a fluorescence image may be generated at the same time.

Figure 11:
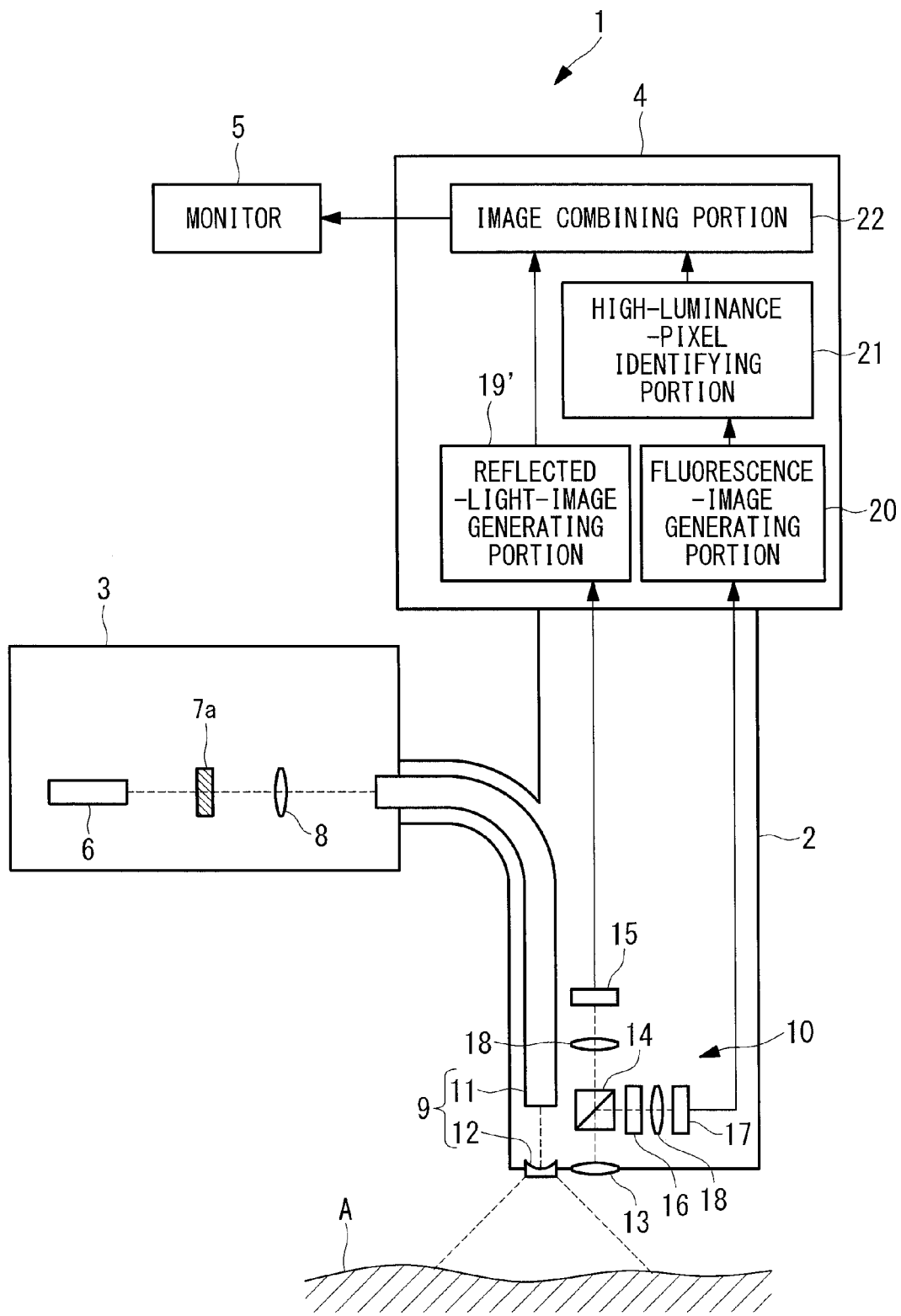
FIG. 11 is a diagram showing the overall configuration of a first modification of the fluorescence observation apparatus in FIG. 1.

For example, as shown in FIG. 11, the light-source unit 3 is provided with an excitation filter 7a that extracts the excitation light from the white light emitted from the xenon lamp 6 instead of the filter unit 7, and the timing controlling portion 23 is omitted in the image processing portion 4. In this configuration, the color CCD 15 captures reflected light of the excitation light that is reflected at and returns from the surface of the examination subject A. Reflected-light-image information acquired by the color CCD 15 is input to a reflected-light-image generating portion 19', which is provided instead of the white-light-image generating portion 19, and a reflected-light image is generated thereat.

Because the reflected-light image is acquired by capturing the reflected light that is reflected at and returns from the surface of the examination subject A, as with the white-light image, it is an image showing the morphological characteristics at the external surface of the examination subject A. Therefore, even if the reflected-light image based on the excitation light is used in this way instead of the white-light image, it is possible to achieve the same advantages as in the first to third embodiments. In addition, by generating the reflected-light image and the fluorescence image at the same time, it is possible to enhance the frame rate of these images.

Figure 12:
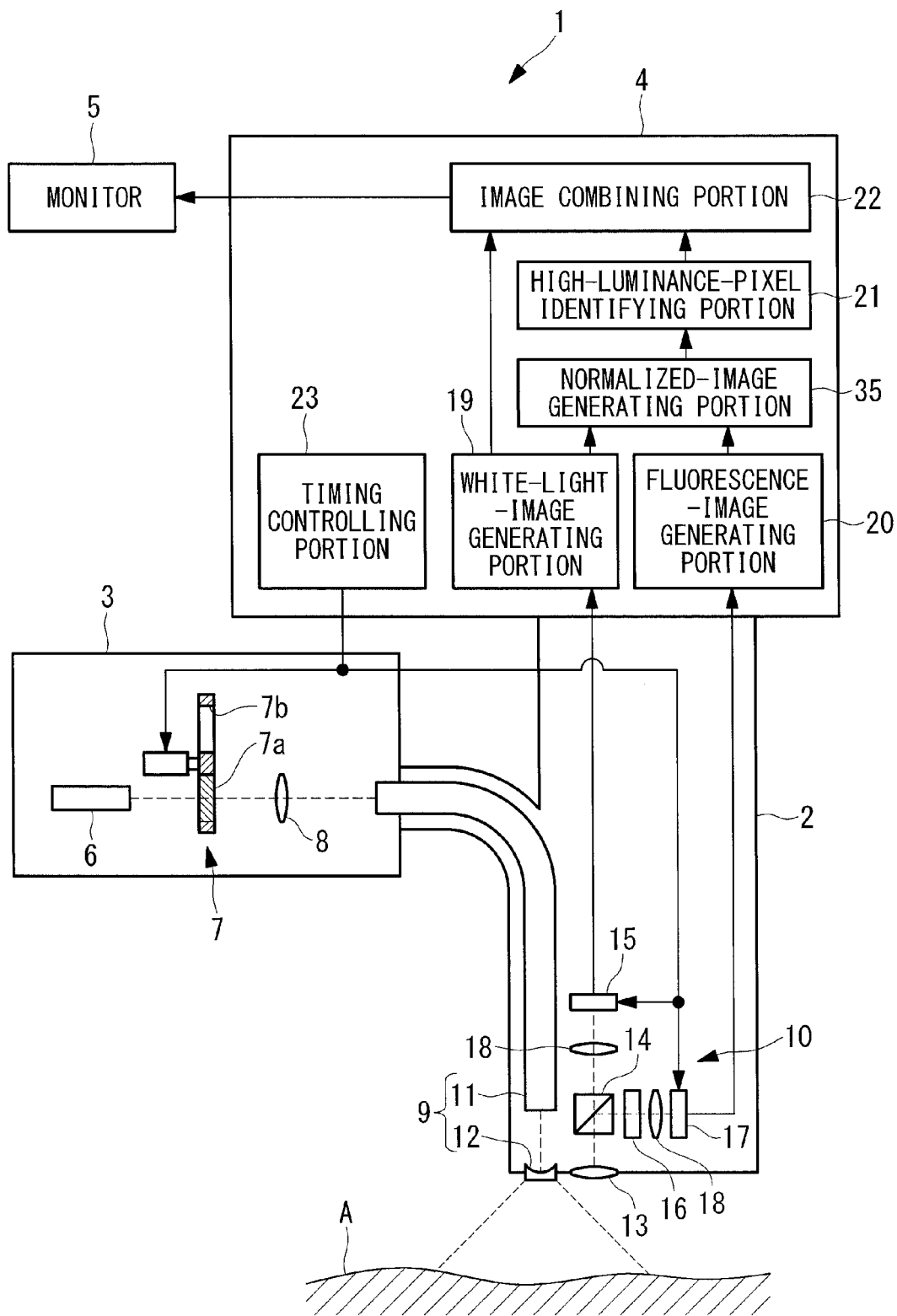
FIG. 12 is a diagram showing the overall configuration of a second modification of the fluorescence observation apparatus in FIG. 1.

In addition, in the individual embodiments described above, the high-luminance pixels are identified in the fluorescence image itself generated by the fluorescence-image generating portion 20; alternatively, however, as shown in FIG. 12, a normalized-image generating portion 35 that generates a normalized fluorescence image by dividing the fluorescence image generated by the fluorescence-image generating portion 20 by the white-light image generated by the white-light-image generating portion 19 may be provided, and the high-luminance pixels may be identified in the normalized fluorescence image. By doing so, fluctuations of fluorescence intensity that depend on the distance and angle of the inserted portion 2 with respect to the examination subject A are normalized, and thus, it is possible to detect cancer tissue with high precision based on a fluorescence-intensity distribution with greater objectivity.

Figure 13:
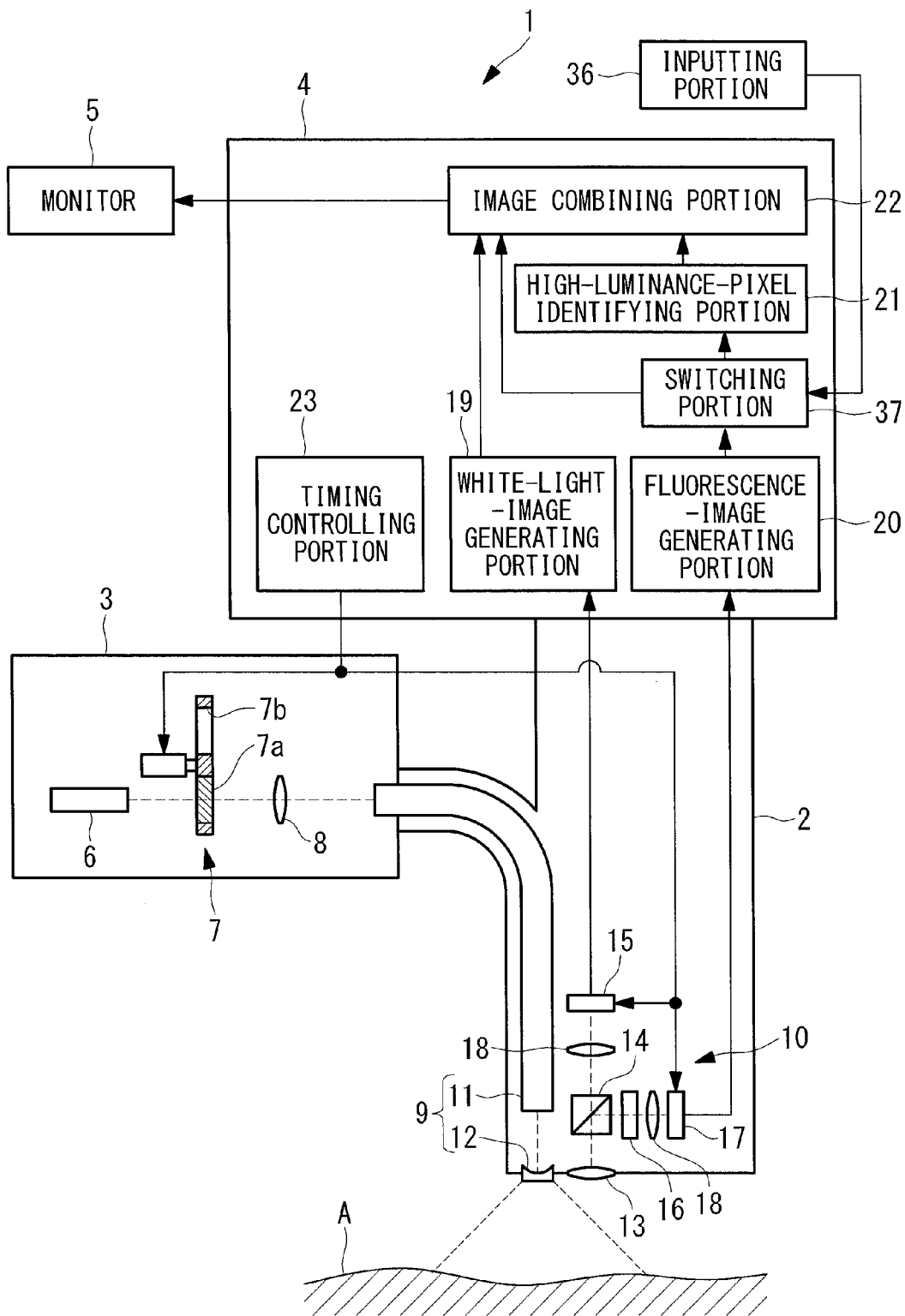
FIG. 13 is a diagram showing the overall configuration of a third modification of the fluorescence observation apparatus in FIG. 1.

In addition, as shown in FIG. 13, the individual embodiments described above may be provided with an inputting portion 36 that takes the form of a switch or the like that is operated by an operator and a switching portion 37 that, depending on input results from the inputting portion 36, switches between superimposing the fluorescence image on the white-light image without modification and superimposing the high-luminance pixels identified in the fluorescence image on the white-light image.

Figure 14:
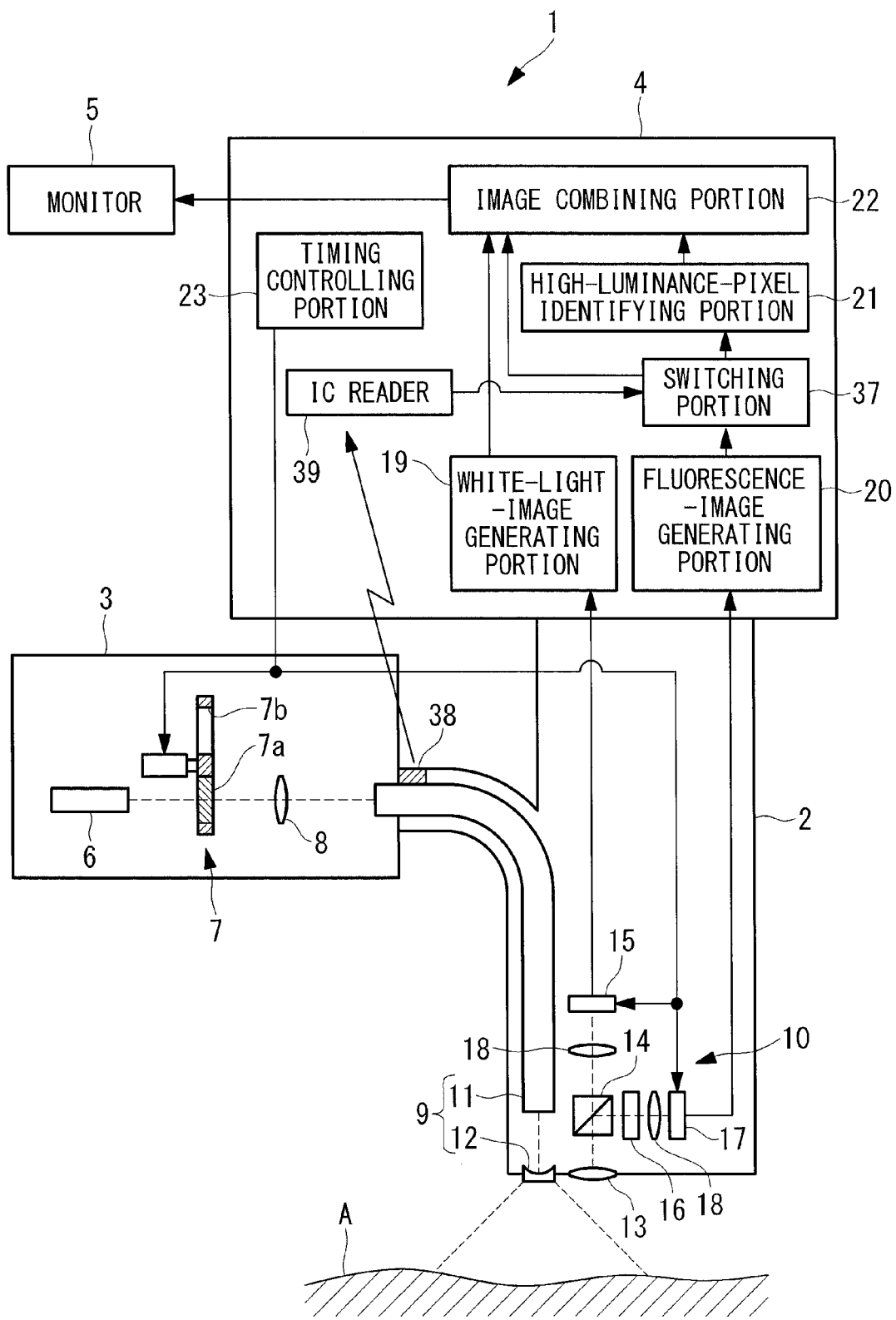
FIG. 14 is a diagram showing the overall configuration of a fourth modification of the fluorescence observation apparatus in FIG. 1.

In addition, as shown in FIG. 14, IC chips 38 that store identification information indicating the types of inserted portions 2 may be provided in inserted portions 2 that are attached to and detached from the image processing portion 4 depending on the observation conditions, and an IC reader 39 that is connected to the switching portion 37 may be provided in the image processing portion 4; and the image to be superimposed on the white-light image may be switched between the fluorescence image and the high-luminance pixels depending on the identification information of the inserted portion 2 read by the IC reader 39. For example, when an inserted portion 2 for mainly observing areas in the vicinity of the liver is mounted, the image to be superimposed should be switched so that the high-luminance pixels identified in the fluorescence image are superimposed, and, in other cases, the image to be superimposed should be switched so that the fluorescence image itself is superimposed.

In addition, although the timing controlling portion 23 is provided in the image processing portion 4, alternatively, it may be provided in the light-source unit 3.

In addition, in the individual embodiments described above, hemoglobin contained in blood has been described as an example of a specific biological component whose concentration in a lesion, such as cancer tissue or the like, is lower than in the other portions; alternatively, however, other types of biological components, such as β-carotene, collagen, vitamins, and so forth, may be utilized.

Figure 15:
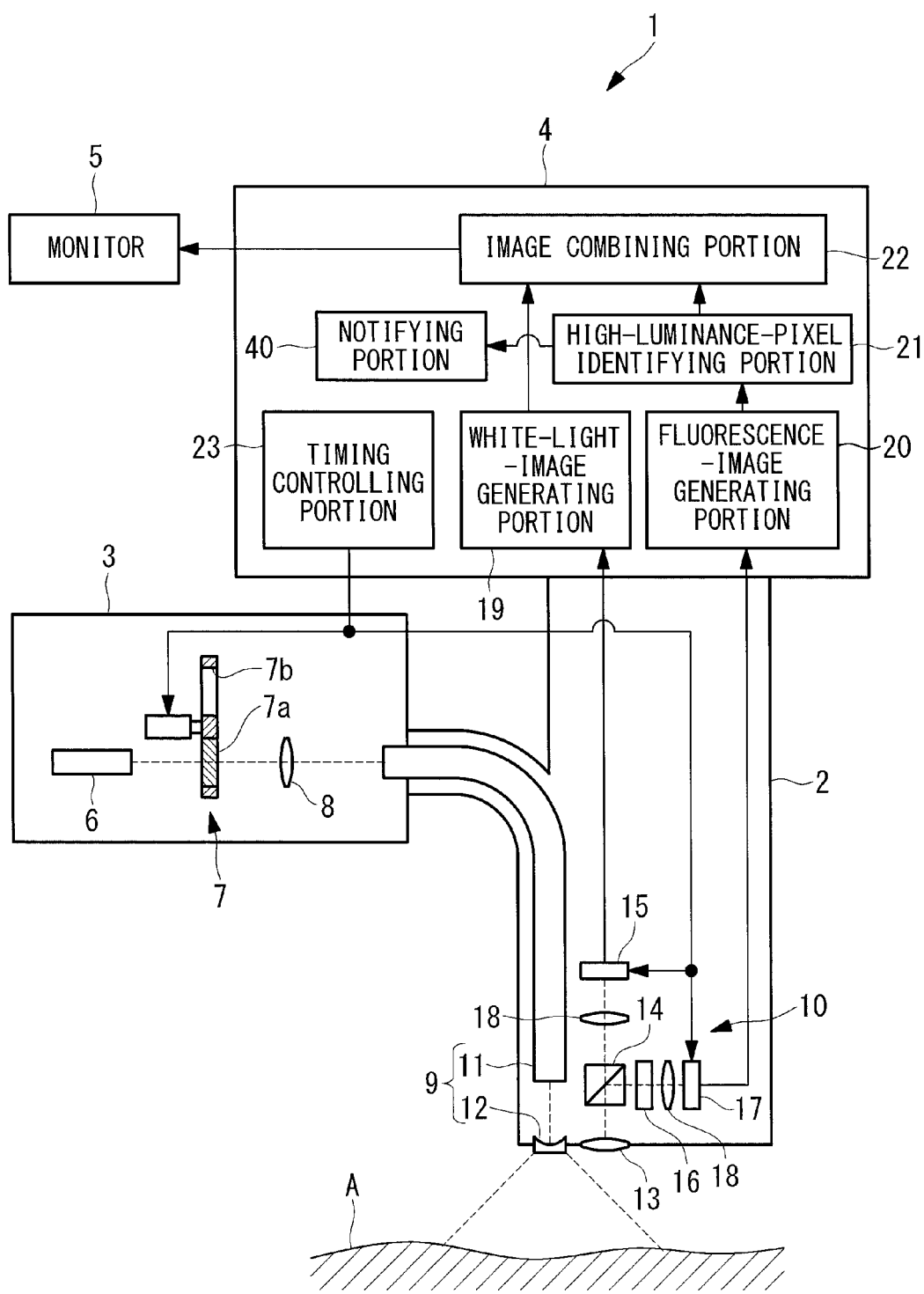
FIG. 15 is a diagram showing the overall configuration of a fifth modification of the fluorescence observation apparatus in FIG. 1.

In addition, as shown in FIG. 15, a notifying portion 40 that issues, in the case in which the high-luminance pixels exist in an acquired fluorescence image, a notification to that effect may be provided. In addition, in the case in which the high-luminance pixels do not exist in a fluorescence image, the notifying portion 40 may issue a notification to that effect. By issuing the notification indicating the presence or the absence of a specific region by means of the notifying portion 40, an observer can easily recognize the presence/absence of a lesion. As a notifying portion 40, a unit that issues a notification by an arbitrary method, such as an image, text, voice, audio, or the like, may be employed.

In addition, in the individual embodiments described above, although CCDs have been described as examples of image acquiring portions, alternatively, any other type of devices such as CMOS imagers and spectroscopic elements may be employed.

REFERENCE SIGNS LIST

A examination subject
1, 1', 1" fluorescence observation apparatus
3 light-source unit (light radiating portion)
5 monitor (display portion)
9 illumination optical system
15 color CCD (reference-light-image acquiring portion)
16 fluorescence filter (non-target-region excluding portion)
17 monochrome CCD (fluorescence-distribution acquiring portion, fluorescence-image acquiring portion)
19 white-light-image generating portion (reference-image acquiring portion)
20 fluorescence-image generating portion (fluorescence-distribution acquiring portion, fluorescence-image acquiring portion)
21 high-luminance-pixel identifying portion (judging portion, identifying portion)
30 color CCD (fluorescence-distribution acquiring portion, fluorescence-image acquiring portion, imaging device)
33 non-target-region excluding portion
34 region setting portion
35 normalized-image generating portion (normalized-fluorescence-image generating portion)
40 notifying portion

The invention claimed is:

1. A fluorescence observation apparatus comprising:
a light radiating portion that radiates excitation light onto an examination subject;
a fluorescence-distribution acquiring portion that acquires an intensity distribution of fluorescence generated at the examination subject due to irradiation with the excitation light from the light radiating portion;
a non-target-region excluding portion that excludes a region, in the examination subject, in which the intensity distribution of fluorescence which is generated satisfies a predetermined condition which is according to a concentration of a specific biological component; and
an identifying portion that identifies a region, as a specific region, which is other than the regions excluded by the non-target-region excluding portion and in which fluorescence whose fluorescence intensity is equal to or greater than a predetermined threshold is generated,
wherein the fluorescence-distribution acquiring portion is provided with an imaging device that includes a plurality of pixels arrayed in rows and columns and that captures the fluorescence, and
wherein the fluorescence observation apparatus further comprises:
a region setting portion that excludes, from among the individual pixels at least in every other row or at least in every other column in the imaging device, a pixel which captures fluorescence whose intensity in equal to or less than a specific wavelength band is decreased, identifies, from among pixels other than the pixels that have been excluded, a pixel which captures fluorescence whose fluorescence intensity is equal to or greater than the predetermined threshold, and, subsequently sets a plurality of pixel groups each of which includes the identified pixel and a plurality of pixels in the surroundings thereof,
wherein the non-target-region excluding portion excludes, in each of the plurality of pixel groups, a pixel which captures fluorescence whose intensity in a wavelength band equal to or less than a specific band is decreased, and
wherein the identifying portion identifies a pixel which is other than the pixels excluded by the non-target-region excluding portion and which captures fluorescence whose fluorescence intensity is equal to or greater than the predetermined threshold.

2. The fluorescence observation apparatus according to claim 1,
wherein the light radiating portion radiates excitation light and reference light onto the examination subject, and
wherein the fluorescence observation apparatus further comprises:
a reference-image acquiring portion that acquires a reference image by capturing return light returning from the examination subject due to irradiation with the reference light from the light radiating portion; and
a display portion that displays a superimposed image formed of the specific region identified by the identifying portion and the reference image acquired by the reference-image acquiring portion.

3. The fluorescence observation apparatus according to claim 1, further comprising:
a judging portion that judges whether or not the specific region having a fluorescence intensity equal to or greater than the predetermined threshold exists in a region other than the regions excluded by the non-target-region excluding portion.

4. The fluorescence observation apparatus according to claim 3, further comprising:
a notifying portion that issues, when the judging portion judges that the specific region exists, a notification to that effect.

5. The fluorescence observation apparatus according to claim 3, further comprising:
a notifying portion that issues, when the judging portion judges that the specific region does not exist, a notification to that effect.

6. The fluorescence observation apparatus according to claim 2, further comprising:
a judging portion that judges whether or not the specific region having a fluorescence intensity equal to or greater than the predetermined threshold exists in a region other than the regions excluded by the non-target-region excluding portion.

7. The fluorescence observation apparatus according to claim 6, further comprising:
a notifying portion that issues, when the judging portion judges that the specific region exists, a notification to that effect.

8. The fluorescence observation apparatus according to claim 6, further comprising:
a notifying portion that issues, when the judging portion judges that the specific region does not exist, a notification to that effect.

9. A fluorescence observation method comprising:
a radiating step of radiating excitation light onto an examination subject;

an acquiring step of acquiring an intensity distribution of fluorescence generated at the examination subject due to irradiation with the excitation light in the radiating step;

an excluding step of excluding a region, in the examination subject, in which the intensity distribution of fluorescence which is generated satisfies a predetermined condition which is according to a concentration of a specific biological component; and an identifying step of identifying a region, as a specific region, which is other than the regions excluded by the excluding step and in which fluorescence whose fluorescence intensity is equal to or greater than a predetermined threshold is generated, wherein, in the acquiring step, the fluorescence is captured by an imaging device that includes a plurality of pixels arrayed in rows and columns, wherein the fluorescence observation method further comprises:

a setting step of excluding, from among the individual pixels at least in every other row or at least in every other column in the imaging device, a pixel which captures fluorescence whose intensity in equal to or less than a specific wavelength band is decreased, identifying, from among pixels other than the pixels that have been excluded, a pixel which captures fluorescence whose fluorescence intensity is equal to or greater than the predetermined threshold, and subsequently setting a plurality of groups each of which includes the identified pixel and a plurality of pixels in the surroundings thereof, wherein, in the excluding step, a pixel which captures fluorescence whose intensity in equal to or less than the specific wavelength band is decreased is excluded in each of the plurality of pixel groups set in the setting step, and wherein in the identifying step, a pixel which is other than the pixels excluded by the excluding step and which captures fluorescence whose fluorescence intensity is equal to or greater than the predetermined threshold is identified.

* * * * *